US00PP28899P2

(12) United States Plant Patent
Delabroye

(10) Patent No.: US PP28,899 P2
(45) Date of Patent: Jan. 23, 2018

(54) ***HEUCHERA* PLANT NAMED 'RED PEARLS'**

(50) Latin Name: ***Heuchera* hybrid**
Varietal Denomination: Red Pearls

(71) Applicant: Thierry Delabroye, Hantay (FR)

(72) Inventor: Thierry Delabroye, Hantay (FR)

(73) Assignee: Sandrine Delabroye, Hantay (FR)

( * ) Notice: Subject to any disclaimer, the term of this patent is extended or adjusted under 35 U.S.C. 154(b) by 27 days.

(21) Appl. No.: 14/999,539

(22) Filed: May 20, 2016

(51) Int. Cl.
*A01H 5/12* (2006.01)

(52) U.S. Cl.
USPC ..... Plt./440

(58) Field of Classification Search
USPC ..... Plt./440

CPC ..... A01H 5/02; A01H 5/00; A01H 5/025
See application file for complete search history.

(56) References Cited

PUBLICATIONS

Henriet Plaisir-Jardin Thierry Delabroye's Summer Open Door 2015 retrievd on Jul. 17, 2017, retrieved from the Internet <http://www.plaisir-jardin.com/2015/08/la-porte-ouverte-estivale-2015-de-thierry-delabroye.html> 14 pp.*
Google English translation Henriet 2017, 2 pp.*

* cited by examiner

*Primary Examiner* — June Hwu
(74) *Attorney, Agent, or Firm* — Penny J. Aguirre

(57) ABSTRACT

A new cultivar of hybrid *Heuchera* named 'Red Pearls', characterized by its leaves that are silvery bronze in color, its early blooming flowers that are red in color and its vigorous and healthy plant habit.

2 Drawing Sheets

Botanical classification: *Heuchera* hybrid.
Cultivar designation: 'Red Pearls'.

CROSS REFERENCE TO RELATED APPLICATIONS

This application is co-pending with a U.S. Plant Patent Applications filed for a plant derived from the same breeding program that are entitled *Heuchera* Plant Named 'Pink Pearls' (U.S. Plant Pat. No. 27,530).

BACKGROUND OF THE INVENTION

The present invention relates to a new and distinct cultivar of *Heuchera* of hybrid origin, botanically known as a *Heuchera* and is hereinafter referred to by its cultivar name 'Red Pearls'.

The new cultivar was discovered by the Inventor in Hantay, France, as a chance seedling amongst many different *Heuchera* varieties in a trial plot in May of 2011. The trial plot contained hundreds of cultivars and proprietary seedlings of *Heuchera* from the Inventor's breeding program. The parentage of 'Red Pearls' is therefore unknown. The objectives of the breeding program were to select cultivars that were floriferous with distinct foliage coloration.

Asexual propagation of the new cultivar was first accomplished under the direction of the Inventor by tissue culture initiated with meristem tissue in Rijswijk, The Netherlands in April of 2015. Asexual propagation of the new cultivar by division and tissue culture has shown that the unique features are stable and reproduced true to type in successive generations.

SUMMARY OF THE INVENTION

The following traits have been repeatedly observed and represent the characteristics of the new cultivar. These attributes in combination distinguish 'Red Pearls' as a new and unique cultivar of *Heuchera*.

1. 'Red Pearls' exhibits leaves that are silvery bronze in color.
2. 'Red Pearls' exhibits flowers that are red in color.
3. 'Red Pearls' exhibits an early flowering habit.
4. 'Red Pearls' exhibits a strong and healthy growth habit.

'Red Pearls' can be most closely compared to the cultivars 'Pink Pearls' and 'Pluie de Feu' (not patented). 'Pink Pearls' is similar to 'Red Pearls' in its plant shape and in having an early flowering habit. 'Pink Pearls' differs from 'Red Pearls' in having foliage that is peach in color and in having flowers that are pink in color. 'Red Pearls' is similar to 'Pluie de Feu' in having flowers that are red in color. 'Red Pearls' differs from 'Pluie de Feu' in having a less compact plant habit and in having foliage that is green in color.

BRIEF DESCRIPTION OF THE DRAWINGS

The accompanying colored photographs illustrate the overall appearance and distinct characteristics of the new *Heuchera*. The photographs were taken of a plant two years in age as grown outdoors in a 15-liter container in Boskoop, The Netherlands.

The photograph in FIG. 1 provides a view of the plant habit of 'Red Pearls' in bloom.

Figure 1:
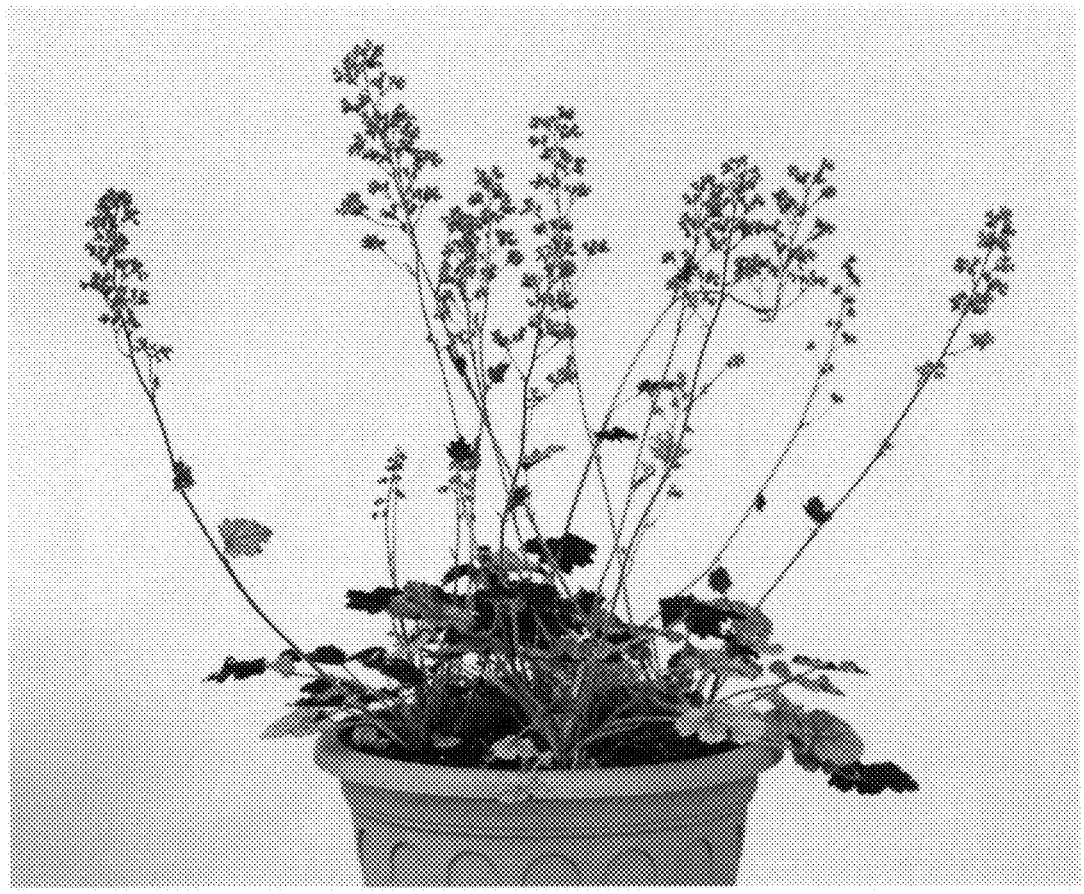
Figure 2:
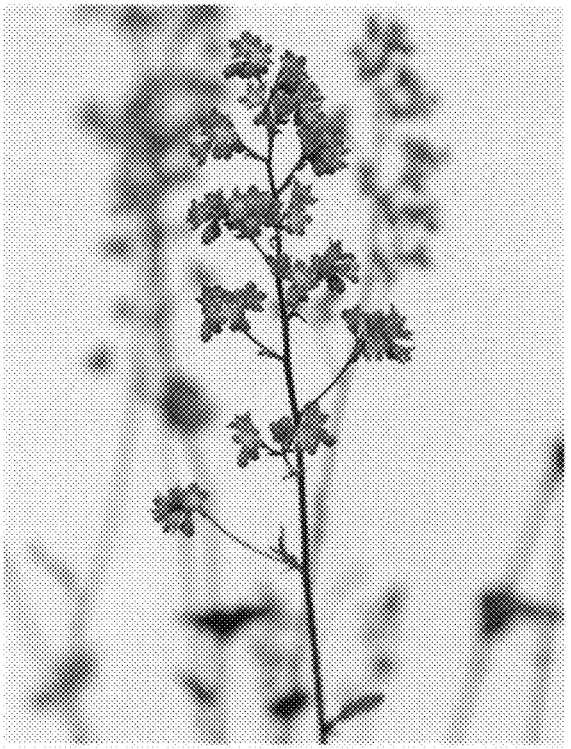

The photograph in FIG. 2 provides a close-up view of an inflorescence of 'Red Pearls'.

Figure 3:
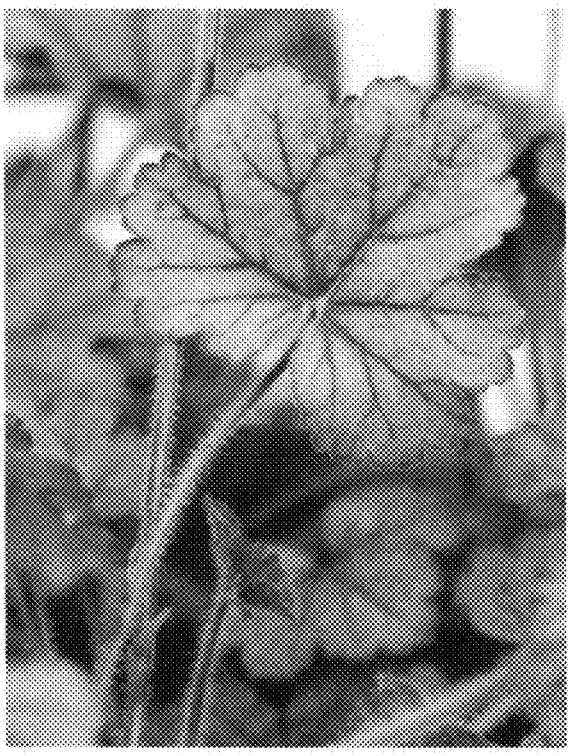

The photograph in FIG. 3 provides a close-up view of the foliage of 'Red Pearls'.

The colors in the photographs are as close as possible with the digital photography techniques available, the color values cited in the detailed botanical description accurately describe the colors of the new *Heuchera*.

DETAILED BOTANICAL DESCRIPTION OF THE PLANT

The following is a detailed description of 2-year old plants of the new cultivar as grown outdoors in 15-liter containers in Hantay, France. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—Early spring to early summer in The Netherlands.

*Plant type*.—Herbaceous perennial.

*Plant habit*.—Clump-forming, mounded foliage.

*Height and spread*.—Average of 13.9 cm in height from soil to top of leaves, 46.8 cm from soil to top of inflorescences, and an average of 42 cm in width.

*Hardiness*.—At least in U.S.D.A. Zones 3.

*Diseases and pests*.—Not more susceptible to pests and diseases than other *Heuchera* varieties.

*Environmental stresses*.—Good sun tolerance with very little to no scorching observed.

*Root description*.—Fibrous roots on woody rootstalks, 163B in color.

*Branching habit*.—Basal rosette, with flowering stems arising from rosettes.

*Propagation*.—In vitro propagation is the preferred method, division are also possible.

*Growth rate*.—Vigorous.

Stem description (peduncle, flowering stem):

*Shape*.—Round.

*Stem color*.—N186D.

*Stem size*.—An average of 1 mm in diameter and 59.9 cm in length.

*Stem strength*.—Moderately strong.

*Stem aspect*.—Flowering stems grow in an average angle of 70° to base (0°=horizontal).

*Stem surface*.—Glabrous, densely covered with short soft hairs, average of 1.5 mm in length, NN155D in color.

*Stem number*.—Average of 15 flowering stems.

Foliage description:

*Leaf shape*.—Broadly ovate to orbicular.

*Leaf division*.—Simple.

*Leaf base*.—Hastate, free to touching.

*Leaf apex*.—Obtuse.

*Leaf venation*.—Laciniate, upper veins; N189A, lower veins; 187B to 187C.

*Leaf margins*.—Lobed with an average of 5 lobes, occasionally 7 per leaf, lobe margins crenate to deeply crenate.

*Leaf attachment*.—Petiolate.

*Leaf arrangement*.—Alternate, basal rosettes.

*Leaf orientation*.—Typically nearly horizontal to slightly hanging.

*Leaf surface*.—Both surfaces slightly glossy and densely covered with short strigose pubescence of hairs an average length of 0.2 cm and N155A in color, average length of hairs on margins and lower side 0.5 cm in length and NN155A in color.

*Leaf color*.—Young upper surface; N186C, slightly tinged 200B, young lower surface; N186D, mature and fall upper surface; 198A, mature and fall lower surface; 187B.

*Leaf size*.—Average of 6.3 cm in length and 6.4 cm in width.

*Leaf quantity*.—12 per basal rosette.

*Petioles*.—Round in shape, average of 13.9 cm in length and 2 mm in diameter, color is 197A, surface densely covered with very short strigose hairs; average of 1.5 mm in length and N155A in color.

*Stipules*.—Small leafy stipules at the base of each leaf, narrow acute apex, with an average of 1.5 cm in length and 5 mm in width and 70A to 70B in color, both surfaces glabrous.

Flower description:

*Inflorescence type*.—Numerous small bell-shaped flowers arranged on pyramidal panicles on flower scapes emerging from the base of the rosette.

*Inflorescence size*.—An average of 16.2 cm in height (excluding peduncle) and an average of 6.6 cm in width.

*Flower fragrance*.—None.

*Flower quantity*.—Average of 100 flowers per flowering stem.

*Flower lastingness*.—Average of one week.

*Flower buds*.—Obovate in shape, an average of 3 mm in diameter and 5 mm in length, 46B, top is 46A.

*Flower aspect*.—Outward to slightly upright.

*Flower type*.—Campanulate.

*Flower size*.—Average of 7 mm in depth (height) and 8 mm in diameter.

*Petals*.—Average of 5, rotate arrangement and implanted in the hypanthium at base, narrow rhomboidal to narrow obovate in shape, margin is entire, apex is acute, upper and lower surface is glabrous and matte, color of upper and lower surface when opening; 54D, color of upper and lower surface when fully open; 53D, petal color fading to 59A on both surfaces.

*Calyx*.—Campanulate, sepals fused to hypanthium, 8 mm in length and 7 mm in diameter.

*Sepals*.—5, fused, campanulate hypanthium, narrow obovate in shape, 8 mm in length and 2.5 mm in width, margin is entire, apex is obtuse to broad acute, fused base, both surfaces are dull and moderately covered with very short glandular hairs about 0.3 mm in length and match the surface color, color: immature upper and lower surface; 46B, mature upper and lower surface; 46A.

*Pedicels*.—Average of 2.5 mm in length and 0.5 mm in width, moderate in strength, color N186C, average angle of 40° (0°=horizontal), surface is glabrous.

Reproductive organs:

*Gynoecium*.—Pistils; 2, average of 3 mm in length, stigmas; pointed in shape, and 158D in color, styles; average of 2.5 mm in length and 155A in color, ovary; 154C in color.

*Androecium*.—Stamens; 5, anthers; ovate in shape, 0.5 mm and 195A in color, filaments; 1.5 mm in length and NN155B in color, pollen is low in quantity and 156A in color.

*Seed/fruit*.—No fruit or seeds observed.

It is claimed:

1. A new and distinct cultivar of hybrid *Heuchera* plant named 'Red Pearls' as herein illustrated and described.

* * * * *